United States Patent [19]

Reeves

[11] Patent Number: 5,337,752
[45] Date of Patent: Aug. 16, 1994

[54] SYSTEM FOR SIMULTANEOUSLY PRODUCING AND SYNCHRONIZING SPECTRAL PATTERNS OF HEART SOUNDS AND AN ECG SIGNAL

[75] Inventor: William Reeves, New Haven, Conn.

[73] Assignee: MCG International, Inc., Branford, Conn.

[21] Appl. No.: 886,627

[22] Filed: May 21, 1992

[51] Int. Cl.[5] ............................................. A61B 5/04
[52] U.S. Cl. .................................................... 128/700
[58] Field of Search ................ 128/696, 700, 701, 710, 128/715

[56] References Cited

U.S. PATENT DOCUMENTS

| | | | |
|---|---|---|---|
| 3,799,147 | 3/1974 | Adolph et al. | 128/715 X |
| 4,226,248 | 10/1980 | Manoli | |
| 4,428,380 | 1/1984 | Wong et al. | 128/715 |
| 4,712,565 | 12/1987 | Katz et al. | 128/715 |
| 4,905,706 | 3/1990 | Duff et al. | 128/701 |

FOREIGN PATENT DOCUMENTS 2188732 10/1987 United Kingdom ................ 128/700

OTHER PUBLICATIONS

Iwata et al., "Algorithm for Detecting the First and Second Heart Sounds by Spectral Tracking", Medical & Biological Engineering and Computing, Jan. 1980 pp. 19–26.

Nilsson et al. "A Combined Microphone for Simultaneous Recording of Pulse, Phono, and Reference ECG", Electromedica #2 64–68 1976.

Primary Examiner—Lee S. Cohen
Assistant Examiner—Jeffrey R. Jastrzab
Attorney, Agent, or Firm—Bachman & LaPointe

[57] ABSTRACT

The present invention relates to a system and a process for detecting, assessing, grading and diagnosing heart conditions in human beings. The system includes a device for providing or generating an acoustic blood flow signal and a signal representative of the electrical activity of a subject's heart. The device for providing the acoustic blood flow (MCG) signal may be a transducer or microphone attached to the patient, or in the alternative, an acoustic signal stored in a storage device. The device for providing the electrical activity (ECG) signal may be an electrocardiogram device attached to the subject or a stored ECG signal. The ECG signal is conditioned in a conditioning circuit to provide a timing or calibration signal having QRS spikes at the onset of each systolic portion of a heart cycle. The MCG signal passes through its own conditioning circuit to filter out unwanted noise and to amplify low frequency sounds. The timing signal and the MCG signal are fed into a microprocessor wherein the MCG signal is converted in a spectral pattern of heart sounds and matched with the timing signal. The output from the microprocessor is a combined, real time MCG pattern/ECG wave signal which may be displayed on a video monitor, which may be put into hard copy form, and/or which may be stored on a storage device.

30 Claims, 10 Drawing Sheets

POWER CABLE

SYSTEM FOR SIMULTANEOUSLY PRODUCING AND SYNCHRONIZING SPECTRAL PATTERNS OF HEART SOUNDS AND AN ECG SIGNAL

BACKGROUND OF THE INVENTION

The present invention relates to a system and a process for detecting, assessing, grading and diagnosing heart conditions in human beings. In accordance with the system and process of the present invention, a spectral phonocardiogram signal and a corresponding electrocardiogram signal are displayed simultaneously, preferably in a synchronized relationship, to facilitate the detection, assessment, grading and diagnosis of a heart condition.

U.S. Pat. Nos. 4,967,760 and 5,012,815, both to Bennett et al., illustrate dynamic spectral phonocardiogram (DSP) systems for generating a spectral phonocardiogram which summarizes time dependent changes in the heart sounds through a heart cycle. The systems are based on the projection of spectral surfaces of the Fourier transform of heart sounds as a function of time. They have been used to screen people for heart disease.

U.S. Pat. No. 4,905,706 to Duff et al. illustrates a similar method and apparatus for detecting coronary artery disease. The Duff et al. system records and analyzes that portion of the phonocardiogram lying between about 100 to 600 Hz. An electrocardiogram is recorded and examined in order to pinpoint the diastolic window of PCG data. This window of data is subjected to autocorrelation analysis and spectral analysis to yield a partial correlation coefficient index and a power density index. A linear combination of these two indices is then used to generate yet another index, termed a Cardiac Screening Index, which is indicative of the presence or absence of coronary artery disease.

The principal disadvantages associated with these systems are that they are limited in scope to dynamic spectral phonocardiograms without any synchronization, which severely limits their clinical utility and application, and to a 2-d phonocardiogram system with electrocardiogram (ECG) which is also severely limited in diagnostic utility because it omits the critical parameters of full frequency and amplitude distribution of heart spectra as a function of time. The Bennett et al. systems, in particular, confine production of spectral patterns to Fast Fourier Transform functions and omit other forms of mathematical approaches which are capable of providing a spectral pattern with adequate resolution for diagnostic purposes.

Bennett et al.'s DSP system is further limited by its time resolution in distinguishing first heart sound (systolic function) from second heart sound (diastolic function) and the critical timing of murmur spectra which has a direct bearing on the valvular source of the murmur. This deficiency is especially evident when the murmur is holosystolic, i.e., it appears across the full timing range of the first and second heart sounds, thus totally blotting out any pattern recognition capability for the human eye to discern the systolic or diastolic timing of important murmur spectra.

Accordingly, it is an object of the present invention to provide a system and process for detecting, assessing the cardiac timing of, grading, and diagnosing a variety of valvular and arrythmia conditions.

It is a further object of the present invention to provide a system and a process as above which provides a total picture for enabling rapid assessment of the overall integrity of a heart.

It is still a further object of the present invention to provide a system and a process as above capable of providing automated computer diagnosis of the probable nature of the condition of a heart.

Still other objects and advantages of the present invention will become more apparent from the following description and drawings wherein like reference numerals depict like elements.

SUMMARY OF THE INVENTION

The foregoing objects are attained by the system and process of the present invention. The system and process of the present invention enable a user to detect, assess, grade and diagnose heart related conditions in mammals, particularly humans, via a combined, time dependent set of heart signals, namely an electrical potential (ECG) signal and an acoustic blood flow signal (MCG), in a real time synchronized manner.

In accordance with a preferred embodiment of the present invention, the system simultaneously produces and synchronizes spectral patterns of heart sounds and a corresponding electrocardiogram signal for a subject. To accomplish this, the system includes means such as a mechanical cardiograph (MCG) for providing an acoustic blood flow signal off the chest or appendages of the subject. As used herein, the term "mechanical cardiograph (MCG)" means a device which captures heart sounds non-invasively off the chest or appendages of a subject from which spectral patterns can be created and which can be displayed real time on a display device. The system also includes means such as an electrocardiogram (ECG) for providing a signal which is a summation of electrical cardiac impulses across the chest of the subject, or in the alternative, for providing a previously recorded and stored electrocardiogram for the subject. The system further includes means for conditioning and/or processing the two signals and means for simultaneously presenting or displaying a combined ECG wave/MCG pattern in a real time manner. In a preferred embodiment, the two signals are processed so that they are presented in a synchronized manner.

The system of the present invention further includes means for allowing a user to listen to the heart sounds as he sees the combined ECG/MCG wave in real time on a video screen and means for storing the ECG/MCG wave signals in digital form for archival and patient history information purposes. Other features of the system of the present invention include a means for providing a user with a printout of the ECG/MCG wave signals if desired and means for providing automated computer diagnosis of the probable nature of a heart condition.

The process of the present invention broadly comprises providing a first acoustic signal of a subject's heart sounds, providing a second signal representing the electrical activity of the subject's heart, conditioning the second signal to obtain a calibration signal with spikes at the onset of each systolic cycle of the subject's heart, processing the first signal to obtain a spectral pattern of heart sounds, and matching the processed acoustic signal with the calibration signal so as to produce a simultaneous display of a spectral heart sound pattern with an electrical activity signal such as a full wave electrocardiogram.

The system and process of the present invention are advantageous in that they provide a physician or user with an "overall picture" of the subject's heart and the ability to both visually and audibly detect abnormal blood flow sounds through the heart in a highly sensitive manner as a function of timing and frequency using an MCG. A user is also provided with the ability to pick out abnormal electrical signals and impulses throughout the same set of cardiac cycles using a synchronized ECG wave. This approach allows a user to highlight interactive cardiac defects where a mechanical problem in turn causes an electrical disfunction, or vice versa.

The system and process of the present invention, which couple audio and video outputs of heart sounds, extend the sensitivity of the human ear and provide a visual wave which allows the human eye to recognize normal and abnormal patterns for rapid detection and diagnosis of blood flow defects within the heart and major blood vessels. Still further, cardiologists and generalists are greatly aided in auscultating specific cardiac defects as well as assessing a patient's overall health. For medical students learning heart sounds, auscultation and physical diagnosis, the system and process of the present invention may be used as a powerful learning tool.

The system and process of the present invention are also very useful as a complementary test to echocardiography for detecting and grading valvular disfunctions, especially since echo is attainable in only 75% of patients, is time consuming to administer, and requires intensive technician training.

An MCG/ECG test such as that provided by the system of the present invention is rapid and easy to use and provides a physician with a hard copy record of the heart sounds and the electrical activity of the subject's heart for archiving and tracking of the subject's valvular condition, whether degenerative or regenerative. The MCG/ECG combined test provided by the system of the present invention is a rapid and effective system for non-specialists to detect and grade valvular blood flow defects and for anesthesiologists and surgeons to rapidly assess cardiac integrity and to gauge preoperative risk and postoperative recovery.

Other features and advantages of the present invention will be discussed in greater detail in the following description.

DETAILED DESCRIPTION

Figure 1:
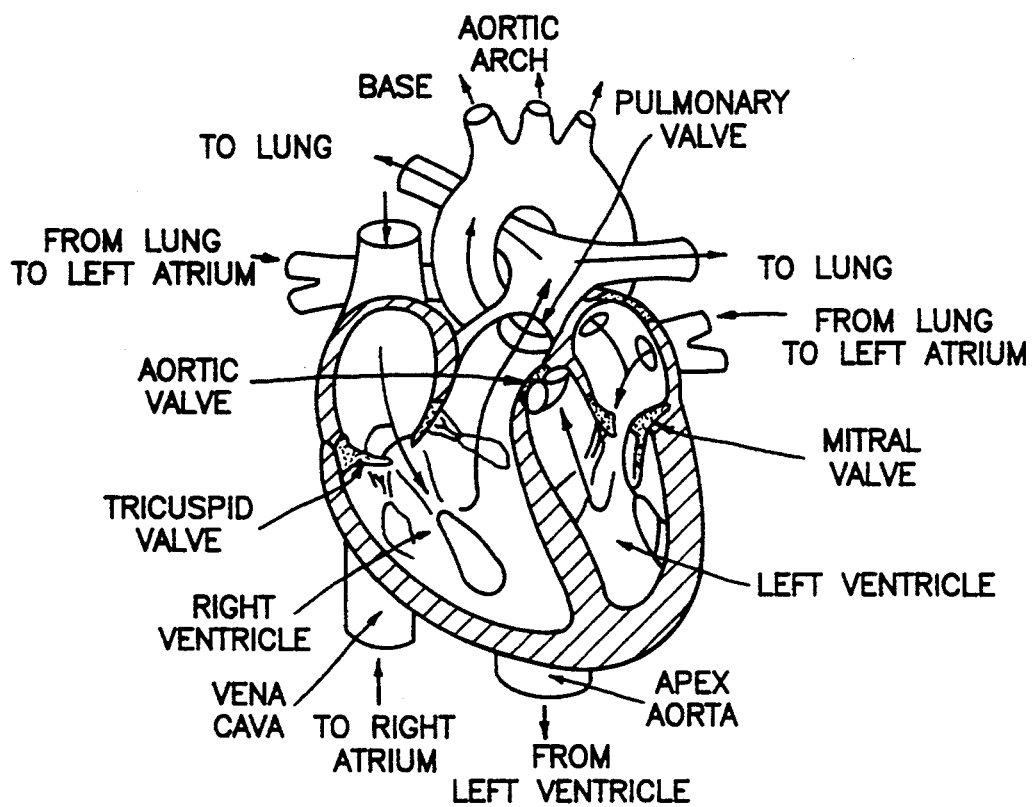
FIG. 1 is a schematic drawing of the human heart showing the basic geometry, direction of blood flow, and valve locations.

Referring now to the drawings, FIG. 1 is a cross-sectional drawing of a human heart. The path of blood flow through the normal heart is shown by the heavy arrows and the four valves are indicated in large bold print. Blood flows in through the vena cava to the right atrium, through the tricuspid valve to the right ventricle, and through the pulmonary valve to the lungs. Blood returning from the lungs enters the left atrium, flows through the mitral valve to the left ventricle, and through the aortic valve to the aorta.

The "First Sound" (S1) in the heart cycle is normally strongest in the apex region, occurs when the heart contracts, and is primarily due to the near simultaneous closing of the tricuspid and mitral valves. During this contraction, blood flows from the right ventricle through the pulmonary valve to the lungs and from the left ventricle through the aortic valve to the aorta. The width of the pulse varies with spectral response function, but typically ranges from about 70 to 100 msecs with A-weighting.

The "Second Sound" (S2) is strongest in the base region, occurs when the heart expands, and is primarily due to the aortic and pulmonary valves closing. During this expansion, blood flows from the right atrium through the tricuspid valve to the right ventricle and from the left atrium through the mitral valve to the left ventricle. The width of the pulse again varies with spectral response function, but typically about 25 to 60 msecs with A-weighting.

The separation between the first (S1) and second (S2) sounds is typically about 300 msecs. The ideal heart sound observed with A-weighing consists of two smooth pulses with durations of about 80 and 40 msecs separated by about 300 msecs over a typical one second heartbeat cycle. These sounds give rise to smoothly-shaped pulses in the frequency domain which could be well resolved as a function of time. However, this result for the normal heart sound requires laminar flow of blood through the valves, heart chambers and blood vessels, as well as simultaneous closure of the two pairs of valves generating the first and second sounds.

Marked departures from the normal heart sound can arise in a variety of ways. There are characteristic recognizable patterns in the frequency domain which are analogous to those which have been previously studied in the time-domain through auscultation:

1) Non-simultaneous closure of either pair of valves. This result in a pair of pulses within the first or second sound which shows up in a strong interference pattern in the frequency domain. This effect may arise from benign causes or from pathological ones which result in more complex patterns in different regions of the spectral phonocardiogram (SPG). Because the timing between openings and closures of valves is part of the recorded data, the spectra can be used to diagnose or confirm electrocardiogram findings.

2) Valvular prolapse can result in regurgitation of blood through the valve during that portion of the cycle in which the valve is supposed to be closed. This in turn results in strong turbulence in the blood flow which results in random high frequency noise components.

3) Narrowing (stenosis) of a valve or blood vessel can result in strong low-frequency pulsations ("palpable thrill") at one extreme, as well as higher-frequency turbulence.

4) Miscellaneous—any marked disruption in normal blood flow will produce some characteristic spectral fingerprint. For example, septal defects, systolic click, diastolic snap, pericardial knock, ejection murmurs, diastolic murmurs, and, in general, any form of valvular incompetence will produce some characteristic fingerprint. It may not always be possible to diagnose the specific problem from the Spectral Phonocardiogram; however, abnormalities tend to stand out in the spectral surface plots.

Heretofore, there has been no system which allowed simultaneous display of a real time spectral heart sound pattern and a synchronized electrocardiogram signal to facilitate the detection, assessment, grading, and diagnosis of heart related conditions in human beings.

Figure 4:
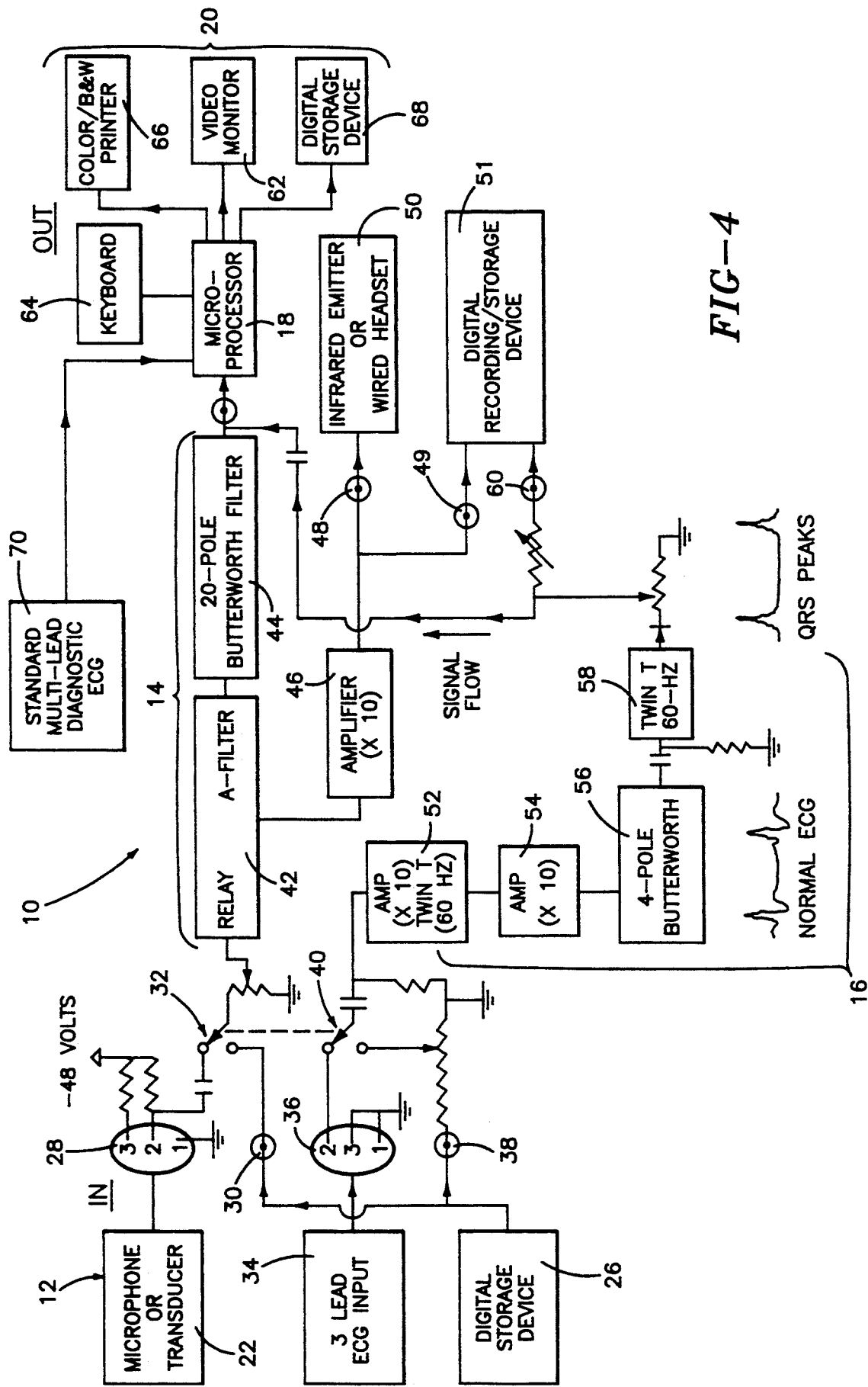
FIG. 4 is a schematic representation of the system of the present invention.

A system 10, in accordance with the present invention, for providing a simultaneous display of a real time spectral heart sound pattern and a synchronized electrocardiogram signal is schematically shown in FIG. 4.

The system 10 broadly includes means 12 for inputting an acoustic blood flow signal (MCG) off a subject and a heart electrical activity signal (ECG) from the same subject, a circuit 14 for filtering and/or conditioning the acoustic MCG signal, a circuit 16 for conditioning the ECG signal, a microprocessor 18, whose function will be described hereinafter, and output devices 20 for displaying, presenting and/or storing a combined signal in a desired form.

Figure 2:
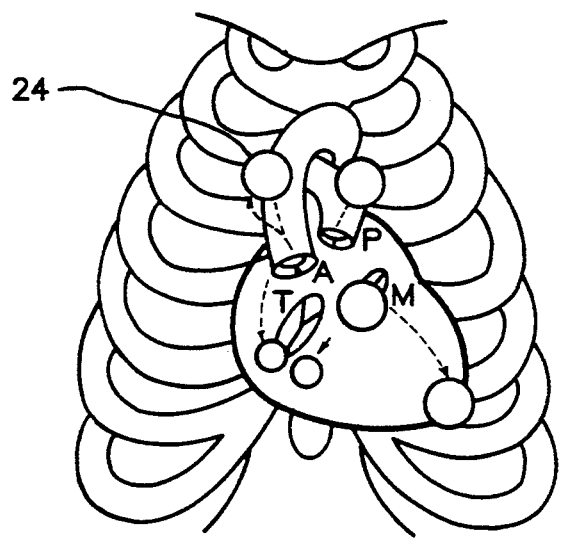
FIG. 2 is an illustration of areas of auscultation of the chest and for placement of a microphone to detect cardiac sounds and murmurs.
Figure 3:
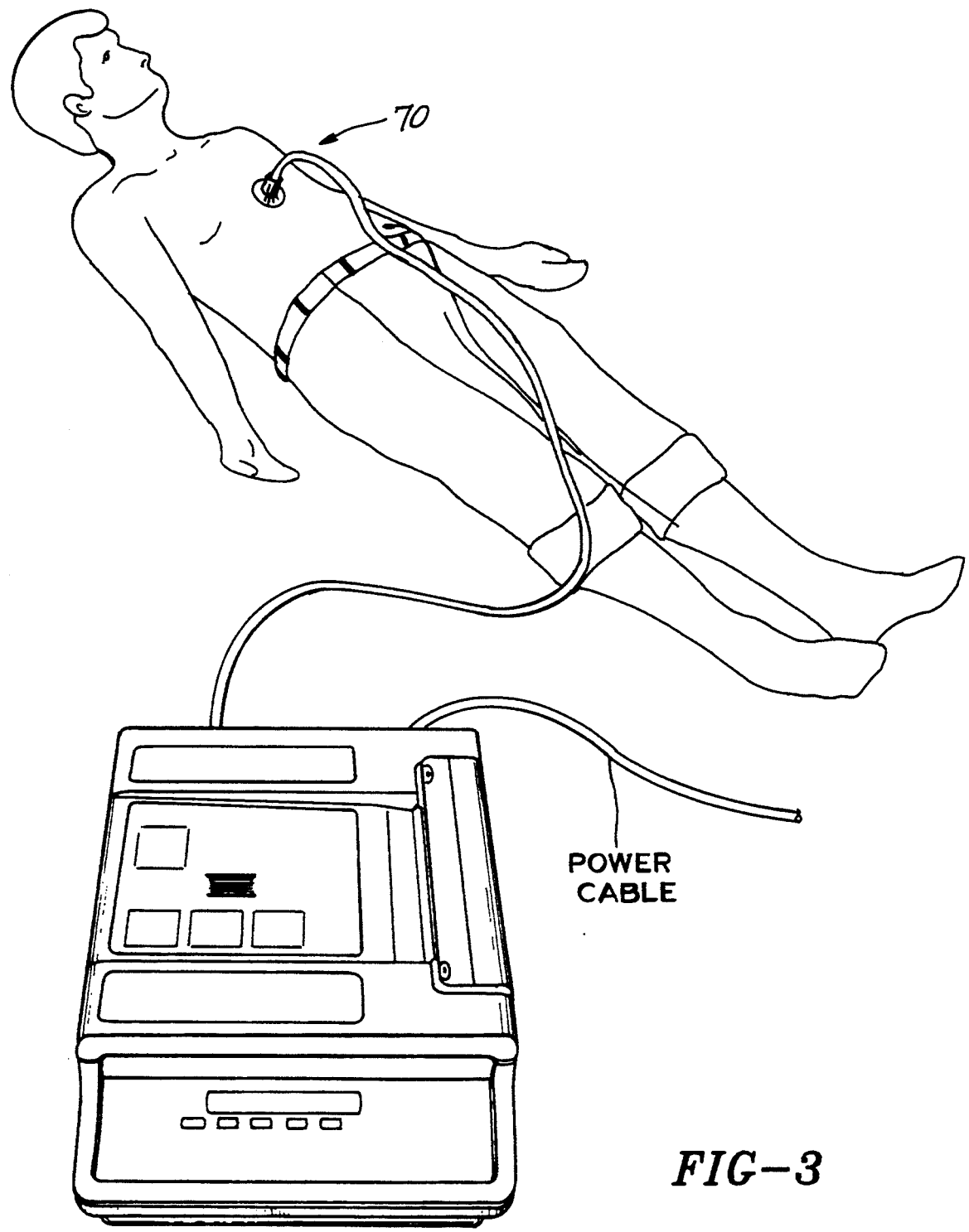
FIG. 3 is an illustration of a human patient connected to an electrocardiograph.

The means for inputting an acoustic signal off the subject into the system 10 may comprise any suitable condensor microphone or transducer 22 known in the art. As shown in FIGS. 2 and 3, the microphone or transducer 22 may be placed in any desired position 24 relative to the aortic valve A, the pulmonic valve P, the tricuspid valve T and the mitral valve M of the subject's heart. Additionally, the microphone or transducer 22 may be secured to the subject's chest using any suitable means known in the art. If desired, more than one microphone or transducer 22 may be employed.

In lieu of a real time acoustic signal, a stored acoustic (MCG) signal of the subject's heart sounds may be inputted from a digital storage device 26. The storage device 26 may comprise any suitable storage device known in the art.

The acoustic signal from a microphone or transducer 22 is fed to an acoustic signal filtering and conditioning circuit 14 of the system 10 via a connector 28 such as a three pin connector, while an acoustic signal stored in the device 26 is fed to the circuit 14 via a jack 30. A double pole, multi-throw switch 32 is provided to allow a user to select either a real time MCG input off a subject or a stored MCG input from the storage device.

The source of the electrical activity (ECG) signal to be inputted into the system may be either a real time electrocardiogram input 34 or an electrocardiogram signal stored in the device 26. The real time electrocardiogram signal may be obtained using any suitable means for taking an electrocardiogram known in the art. The (ECG) signal thus obtained is introduced into a conditioning circuit 16 via a connector 36 such as a three pin connector, while the stored electrocardiogram signal can be introduced into the circuit 16 via a jack 38. Once again, a double pole multi-throw switch 40 is provided to allow a user to select between a real time electrocardiogram signal or a stored signal.

Figure 5A:
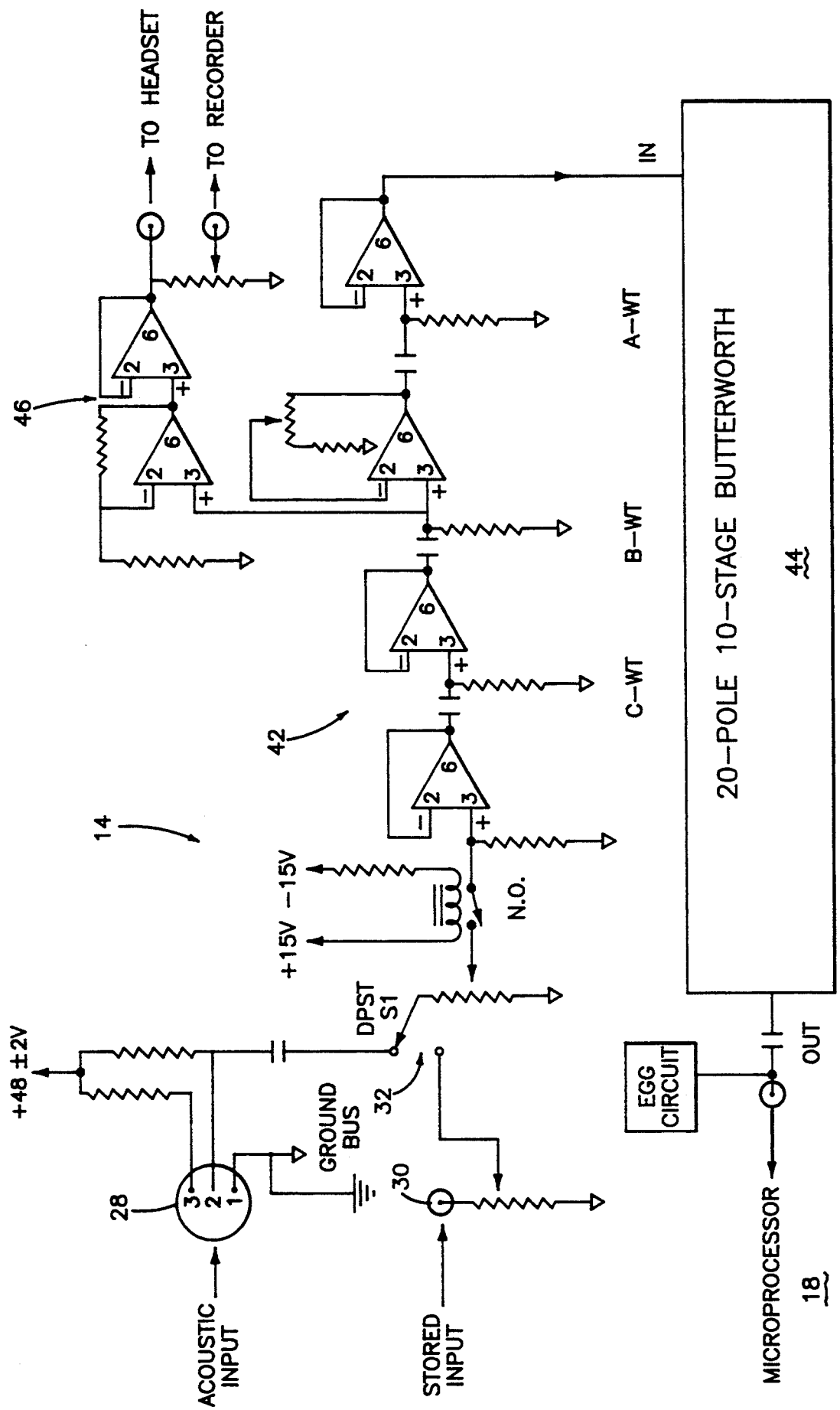
FIG. 5A illustrates a diagram of the acoustic signal conditioning circuit employed in the system of FIG. 4.

As shown in FIGS. 4 and 5A, the acoustic MCG signal is passed through a circuit 14 which may be in either digital or analog form. The circuit 14 includes a filter/amplification device 42 for A-weighing the acoustic signal and removing extraneous background noise. The circuit also includes a 20-pole stepped Butterworth filter 44 for conditioning and anti-aliasing the signal. The Butterworth filter 44 serves to filter out unwanted background noise and highlight the low frequency sound portion of the cardiac cycle. In particular the Butterworth filter magnifies the sensitivity for signals having a frequency in the range of about 50–950 Hz with a sharp roll-off below 50 Hz and above 950 Hz. While any suitable Butterworth filter may be used, it is preferred to use a ten stage filter having an increased resistance value from stage to stage and a steady capacitance to achieve the desired roll-off effect. Suitable resistances for the ten stages are in the range of about 60 ohms at the first stage to about 18,500 ohms at the tenth stage.

The circuit 14 also includes an amplifier 46 connected to the device 42 and an output jack 48 for allowing an infrared emitter or wired headset 50 to be connected to the system so that a physician, scientist or other user can hear the subject's heart sounds as he views a corresponding spectral pattern on one of the output devices 20. If desired, the filtered acoustic signal amplified by amplifier 46 may be saved on a digital recording/storage device 51 via the output jack 49.

As previously discussed, the system 10 includes an ECG conditioning circuit 16. This circuit is designed to produce an ECG calibration QRS spike signal which is used as a trigger pulse or timing signal.

The circuit 16, as shown in FIGS. 4 and 5, may be either digital or analog and is preferably separately grounded from the circuit 14. It includes amplifiers 52 and 54 for suppressing and rejecting 60 Hz noise and harmonics from the ECG signal and for amplifying the inputted ECG signal to a desired level, approximately 10x, and a 4-pole, 2-stage Butterworth filter 56 which acts to cut off all signal noise above 3 Hz. The filter 56 may also remove electrical activity signals during the diastolic portion of the heart cycle and signals resulting from other types of extraneous events which cause electrical activity.

The filtered ECG signal is fed to a differentiation and rectification circuit 58 for removing 60 Hertz and 60 cycle noise and low voltage potential since ECG signals in general are subject to 60 Hz background noise and for suppressing the negative component of the ECG wave. The output of the differentiation and rectification circuit is a timing or calibration signal having only the dominant QRS spikes at the onset of each systolic portion of the heart cycle. The timing signal thus produced is used to synchronize an ECG signal with a spectral pattern formed from the acoustic (MCG) signal. The ECG signal may be a full wave diagnostic ECG pattern or any other diagnostic test signal which includes a full wave diagnostic ECG pattern.

Figure 5B:
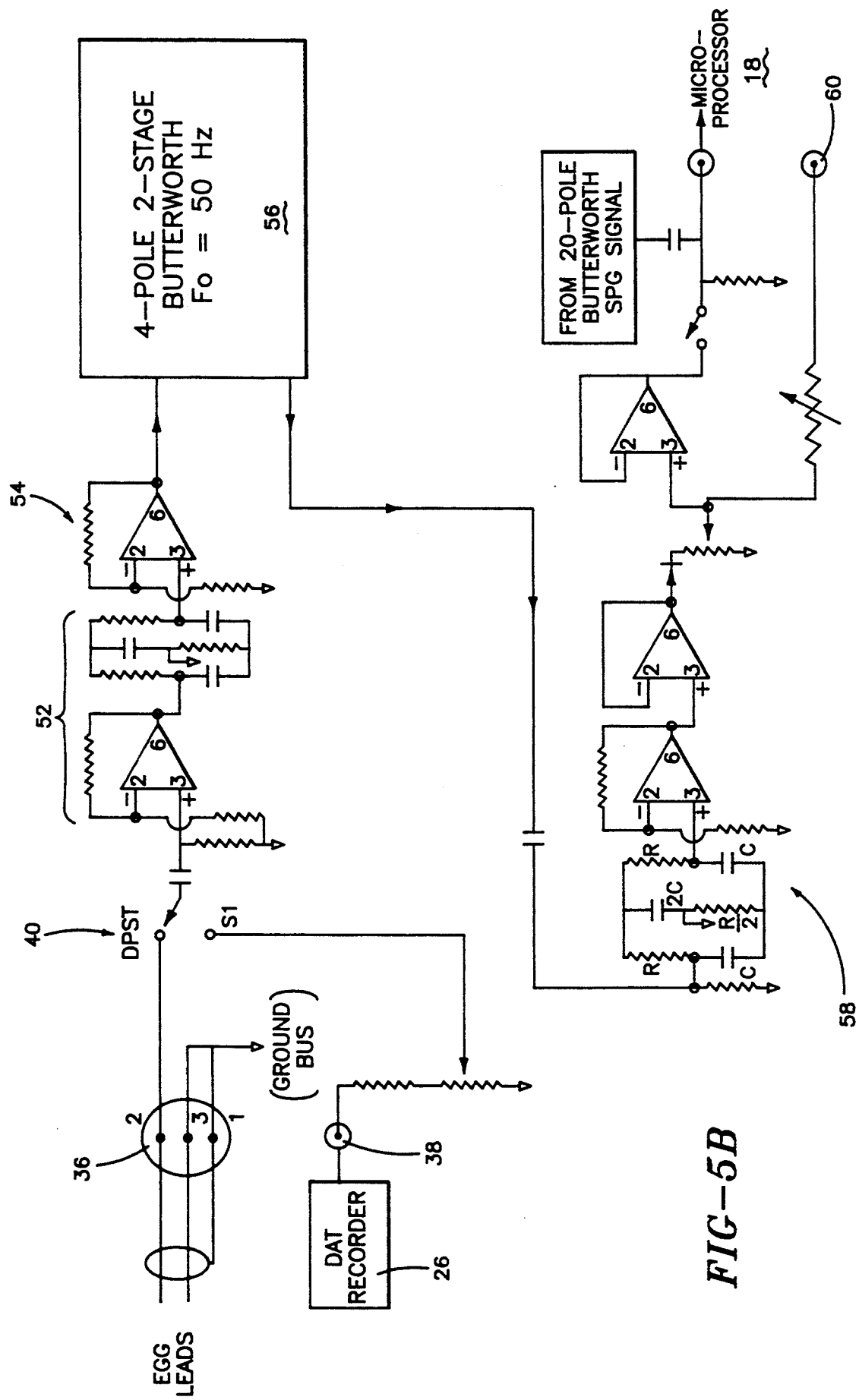
FIG. 5B illustrates a diagram of the ECG conditioning circuit employed in the system of FIG. 4.

As shown in FIGS. 4 and 5B, the timing signal thus produced is fed to the microprocessor 18 along with the conditioned acoustic signal albeit in separate channels. The timing signal is used to correlate a spectral pattern formed from the acoustic signal with the spikes of the ECG signal or the full wave diagnostic ECG pattern in such a way that the two can be synchronized and overlaid upon each other. The timing signal may also be fed to the digital recording/storage device 51 via the jack 60. In this way, acoustic data and the QRS data may be stored together in a synchronized form.

The device 51 may comprise any suitable device known in the art for simultaneously digitally recording both signals on a digital medium for archival and library purposes and for later playback. The information stored on the device 51 may be unprocessed acoustic and ECG output signals from the circuits 14 and 16.

If a multi-lead diagnostic ECG device 70 is connected to the subject, it may be be used to provide a non-conditioned real-time ECG signal to the microprocessor 18. The device 70 may be any standard ECG device known in the art. Alternatively, the device 70 may be omitted if desired.

The microprocessor 18 used in the system 10 may comprise any suitable microprocessor or central processing unit known in the art. Preferably, the microprocessor 18 has two channels, one for the conditioned acoustic signal and a second one for the calibration signal. The second channel may also be used to carry the signal from the ECG device 70.

Figure 5C:
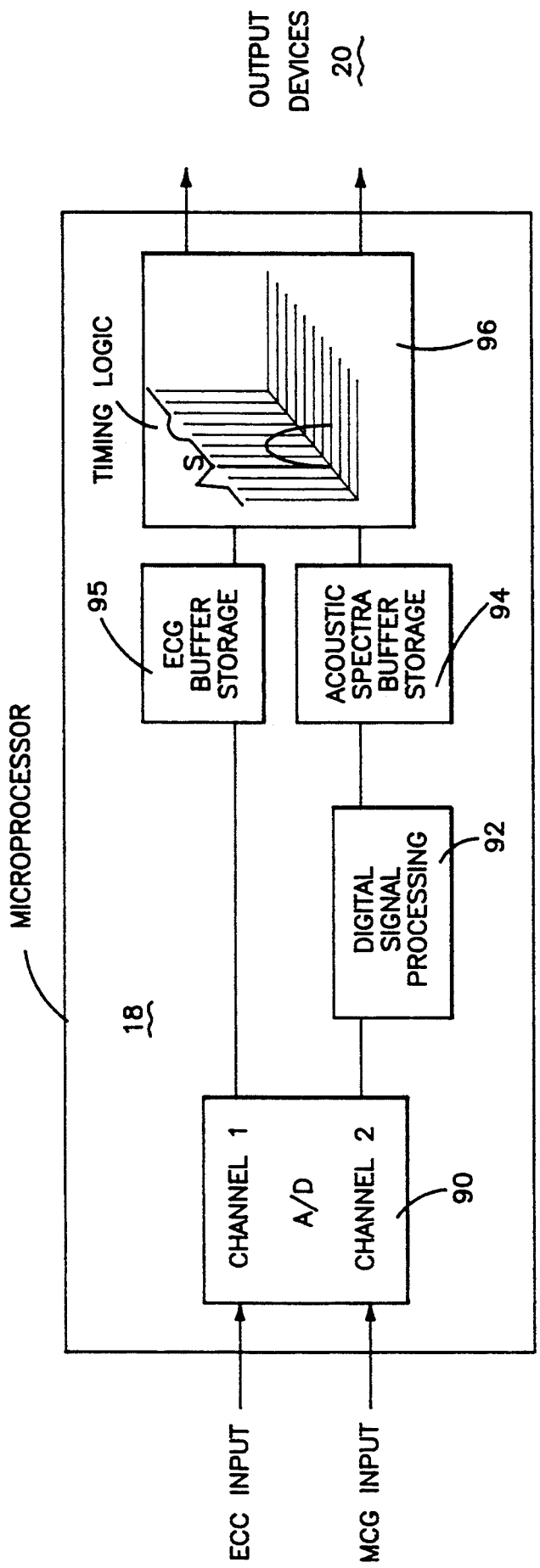
FIG. 5C is a schematic representation of the microprocessor used in the system of the present invention.

As shown in FIG. 5C, the microprocessor includes chip means 90 for converting any incoming acoustic signals and ECG full wave and/or the calibration ECG signal in analog form to digital signals and digital signal processing (DSP) chip means 92 for producing digitized spectral patterns of the acoustic heart signals in a real time processing manner. The ECG full wave and/or the calibration ECG, once converted, are stored sequentially in a memory buffer means 95 within the microprocessor 18. The output from the DSP chip means (92) is stored within a buffer means 94. In this way, heart sound spectra produced by the microprocessor are held in storage by the buffer memory 94 until they can be synchronized and outputted in a coordinated and real time manner. Additionally, the provision of the buffer means 94 makes signal processing speed more efficient and streamlined.

The DSP chip which is employed in the microprocessor may be programmmed to perform a spectral analysis of the acoustic sounds using any suitable technique known in the art for providing a spectral pattern with adequate resolution for diagnostic purposes. Mathematical algorithms for producing spectral patterns of heart sounds which may be programmed into the chip may include Fast Fourier Transforms, the autoregressive covariance method, any variation of the maximum entropy method, the Stieglitz-McBride methods, Welch's method and Gabor transforms (Gabor Spectrogram). These algorithms and techniques are known in the art and exemplified by the articles: "Evaluation of FFT-Based and Modern Parametric Methods for the Spectral Analysis of Bioprosthetic Valve Sounds", by Louis G. Durand et al., IEEE Transactions on Biomed Engineering, vol. 33, No. 6, June 1986, pp. 572–578; "Frequency Spectra of the First Heart Sound and of the Aortic Component of the Second Heart Sound in Patients with Degenerated Porcine Bioprosthetic Valves", by Paul D. Stein et al., American Journal of Cardiology, 1984, No. 53, Feb. 1, 1984, pp. 557–561; "Pole Zero Modeling and Classification of Phonocardiograms", by Tae H. Joo et al., IEEE Transactions on Biomedical Engineering, Vol. 30, No. 2, February, 1983, pp. 110–118; "Real-Time Sound Spectroanalysis For Diagnosis of Malfunctioning Prosthetic Valves", by Yuzuru Kagawa et al., Journal of Thoracic Cardiovascular Surgery, Vol. 79, 1980, pp. 671–679; "Detection of Aortic Porcine Valve Dysfunction By Maximum Entropy Spectral Analysis", by Rodney A. Foale et al., Circulation Magazine, Vol, 68, No. 1, 1983, pp. 42–49; "Estimation of the Severity of Aortic Valve Stenosis by Frequency Analysis of the Murmur", by Gary R. Johnson et al., Journal of American College of Cardiology, Vol. 1, No. 5, 1983, pp. 1315–1323; "Evaluation of Aortic Stenosis by Spectral Analysis of the Murmur", by Gary R. Johnson et al., Journal of American College of Cardiology, Vol. 6, No. 1, July 1985, pp. 55–63; "Continuous Spectral Analysis of Heart Murmurs for Evaluating Stenotic Cardiac Lesions", by Richard L. Donnerstein, American Journal of Cardiology, Vol. 64 Sep. 15, 1989, pp. 625–630: "Theory of Communication", By D. Gabor, Journal of IEE (London), Vol. 93, No. III, Nov. 1946, pp. 429–457; "Orthogonal-Like Discrete Gabor Expansion and Gabor Spectrogram", By S. Qian et al., 26th Conference on Information Sciences and Systems, Mar. 18, 1992, pp 1–5; and "Discrete Gabor Expansions". By J. Wexler et al., Signal Processing, Vol. 21, No. 3, Nov. 1990, pp 207–221, all of which are hereby incorporated by reference herein.

The microprocessor 18 also has timing logic means 96 for matching the acoustic first heart sound (S1) with the first QRS spike of the conditioned ECG signal. The timing logic means 96 may be an analog circuit within the microprocessor or programming within the microprocessor which looks at the first ECG wave stored in the ECG buffer 95 and identifies the S-node of the QRS spike by looking at the peak millivolt signals of the QRS spike and tracing the spike to the S-node. The logic means 96 then enters the MCG buffer 94 and looks at the first heart sound and identifies the onset of the first heart sound by sensing a proportional slope rise in amplitude. The timing logic means 96 then sets the timing of the S-node to the onset of the first heart sound. In this way, the microprocessor synchronizes the spectral pattern of the heart sounds with the conditioned ECG signal and/or a full wave ECG signal.

Figure 6:
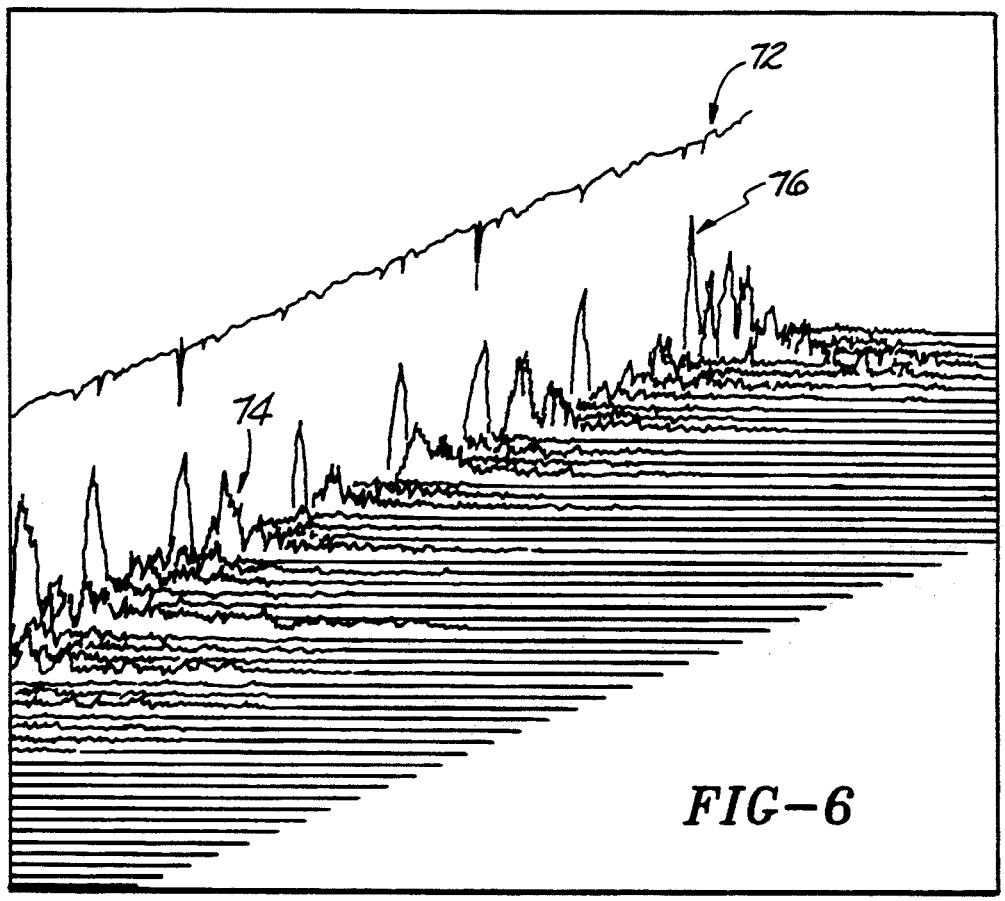
FIG. 6 illustrates a display of a synchronized ECG/MCG wave generated by the system of the present invention.

The synchronized combined signal outputted by the microprocessor 18 in the form of an ECG wave 72, which is synchronized with an MCG pattern 74 and the QRS calibration spikes 76, is a summation of electrical cardiac impulses as measured across the chest. As shown in FIG. 6, it is also a time dependent signal in three dimensional form wherein the three dimensions are time, frequency, and RMS sound pressure.

The synchronized combined output signal may be displayed on a number of different output devices. For example, it may be displayed on a video monitor 62. The video monitor 62 may comprise a high resolution color video monitor, a black and white monitor, or a liquid crystal display.

The synchronized combined output signal may also be displayed on a color or black and white printer 66. In this way, a hardcopy recording of the MCG pattern and the ECG wave can be provided from the video screen. If desired, a keyboard 64 connected to the microprocessor can be used to provide the hardcopy with subject identification, physician's name, date and time information, and other pertinent information. Still further, a digital recording/storage device 68 may be provided to accept the output signals from the microprocessor 18 for archival/library purposes. The device 68 may be a hard drive, a disk drive and diskettes, a laser disk recorder, a tape storage device, a CD ROM device, a chip device, or any other digital storage medium known in the art.

The output from the microprocessor may be displayed on the video monitor 62 as a real time, three-dimensional scrolling spectral pattern of heart sounds along with the QRS spike calibration signal and/or a complete ECG signal. The scrolling may start at the back right hand corner of the monitor and scroll from right to left. The spectral pattern is preferably synchronized with and ECG calibration spike and/or a multi-lead ECG signal which is also scrolling from right to left. This allows the operator to freeze the video screen at any time and read the MCG and ECG data like English from left to right.

Figure 7A:
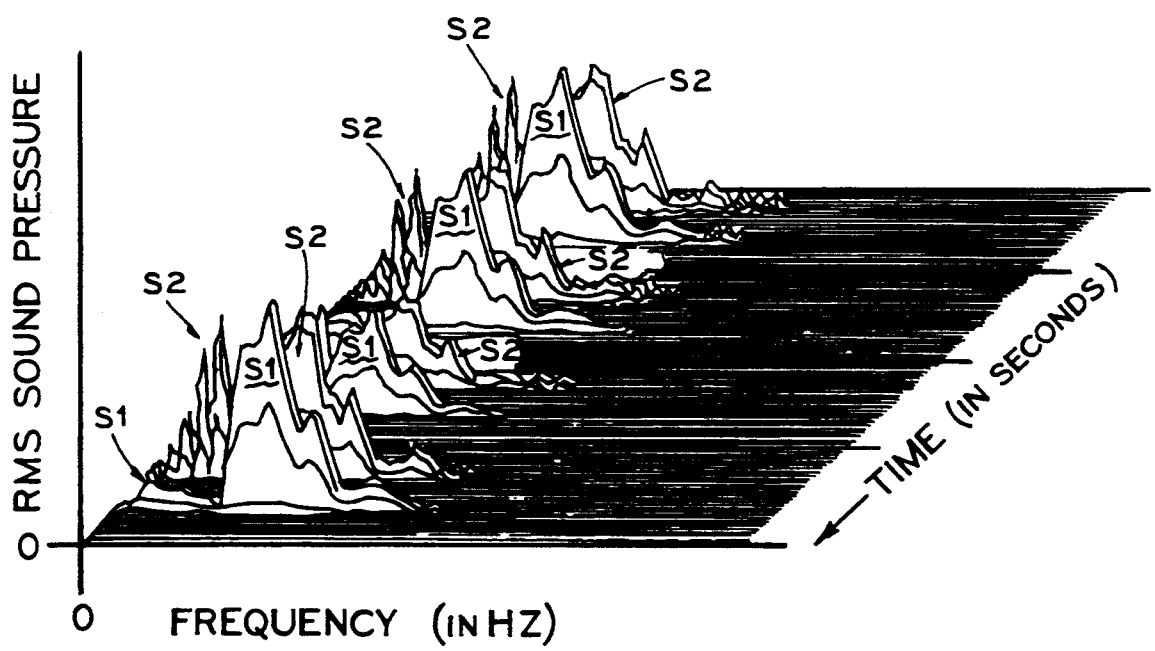
FIGS. 7A through 7D illustrate displays of various outputs from the microprocessor and the system of the present invention.
Figure 7B:
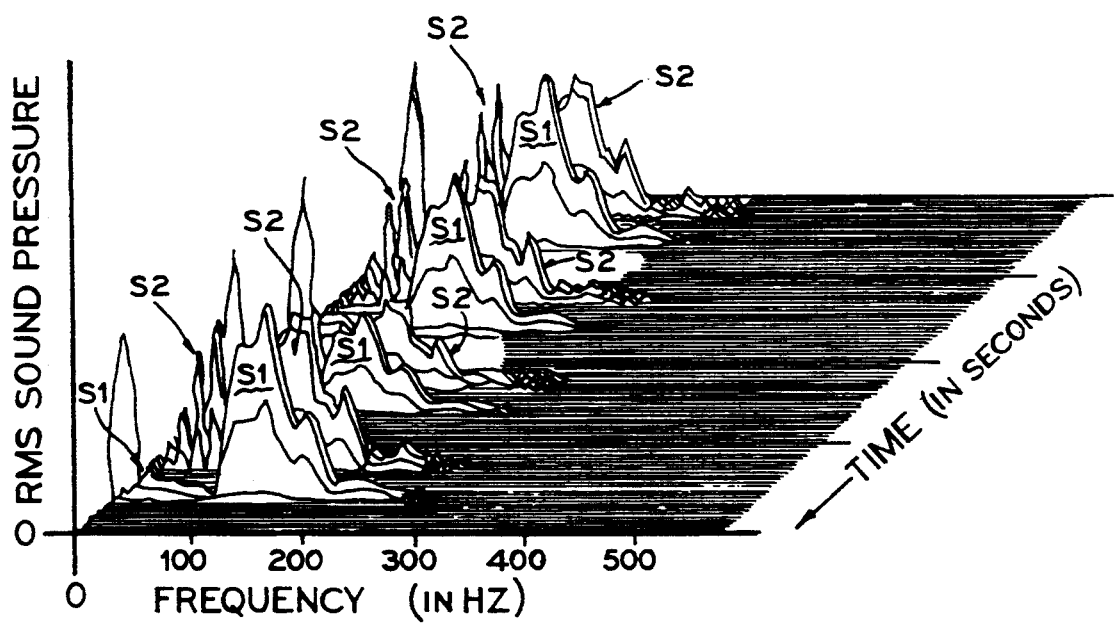
Figure 7C:
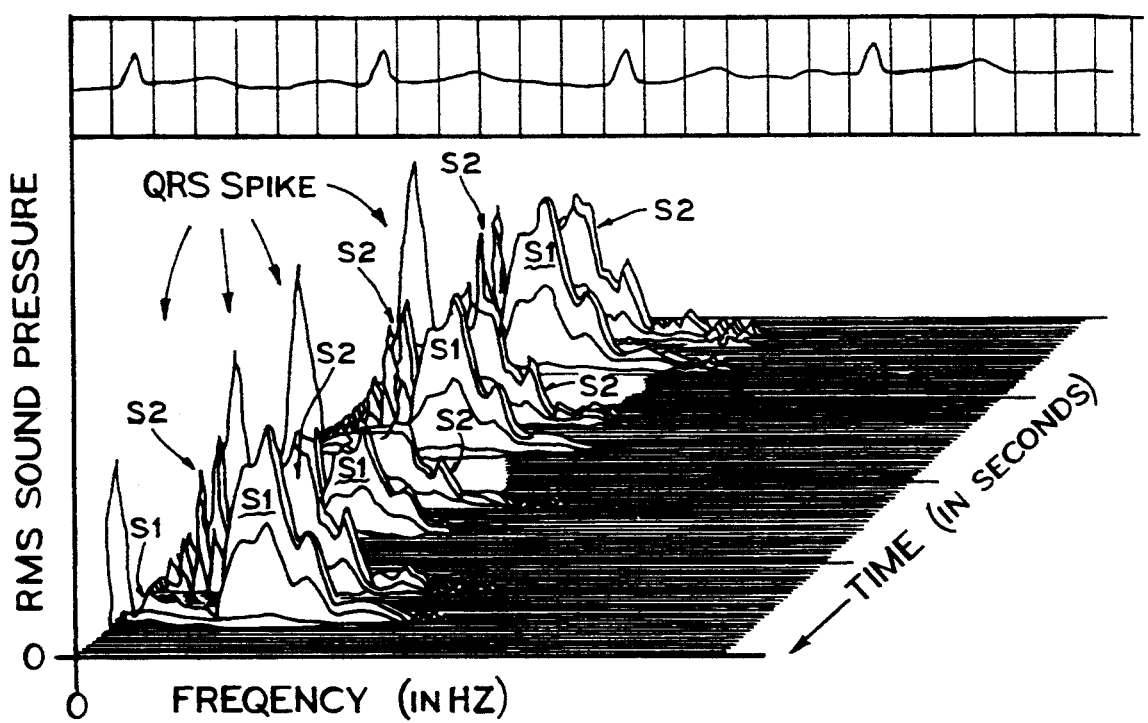

FIGS. 7A through 7D illustrate various output displays which can be generated by the system of the present invention. FIG. 7A illustrates a three dimensional spectral pattern display for a 33 year old male with normal heart sounds taken off the apex of the chest without any ECG or ECG calibration spike. FIG. 7B illustrates a three dimensional spectral pattern display for a 33 year old male, normal heart sounds taken off the apex of the chest which includes the QRS calibration spike. As can be seen from this Figure, the QRS spike is synchronized with the onset of the first heart sound (S1) for four heart cycles. FIG. 7C illustrates a spectral pattern display for a 33 year old male, normal heart sounds taken off the apex of the chest which includes an ECG calibration QRS spike and a normal full wave ECG for the subject.

Figure 7D:
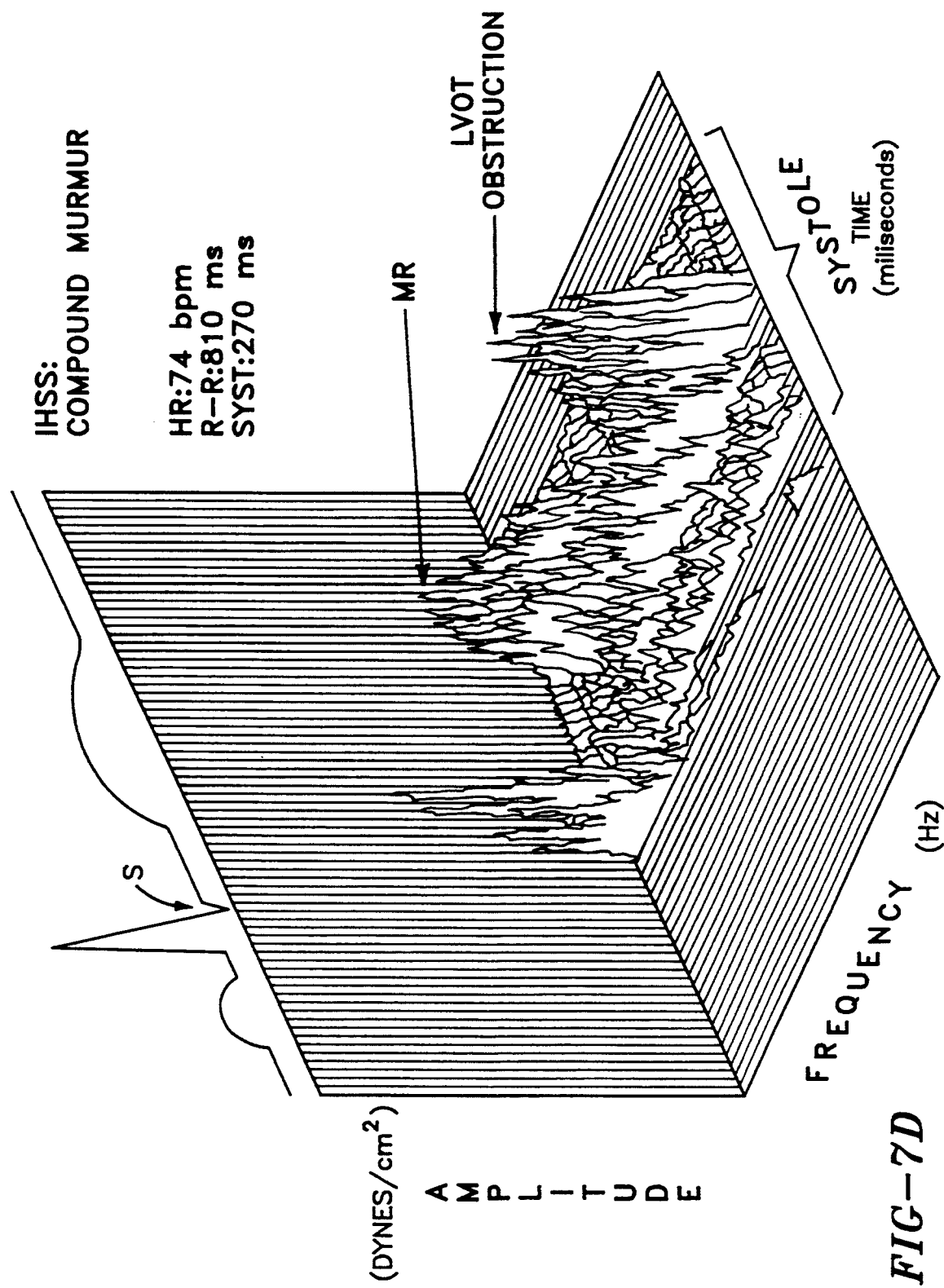

FIG. 7D illustrates a high resolution spectral pattern which can be generated by the system of the present invention. As shown in this figure, the x-axis can be frequency, either in the range of 0–1000 Hz in the case of the examination of natural heart valves or in the range of 0–4000 Hz in the case of examining prosthetic heart valves; the y-axis can be sound pressure in dynes/$cm^2$ or Db; and the z-axis can be time in milliseconds. Each axis may be labelled if desired and calibrated to known scientific standards.

If desired, the amplitude of the sound pressure may be normalized from a patient to patient using auto gain logic means, such as an auto gain circuit, within the microprocessor 18 to account for differences in body fat, sternum and rib construction, and muscle from subject to subject. The calibration of the y-axis may be performed automatically by the auto gain circuit so that the amplification of the acoustic signal is strong enough to register a spectral pattern of sufficient amplitude for viewing and pattern recognition. In order to provide for a uniform and normalized sound pressure scale, the microprocessor controlled gain may also tabulate the scale factor by which the amplitude was increased or decreased from patient to patient. This will provide both a "self normalizing" auto gain circuit and a means to calibrate the sound pressure to known scientific standards.

If desired, the heart rate of the patient may be automatically calculated by the microprocessor 18 using any suitable software from the spectral pattern heart sounds and automatically displayed on the output device. Still further, the microprocessor 18 may calculate the systolic and diastolic timing functions and may determine a preliminary diagnosis using diagnostic software logic installed within the microprocessor. As shown in FIG. 7D, these parameters may be displayed on the output device. For example, the systolic and diastolic timing functions may be displayed as a function of time, i.e., R-R 810 nmilliseconds, syst 270 milliseconds. The diagnosis may be "IHSS, Compound Murmur".

In operation, an acoustic (MCG) signal representing a subject's or patient's heart sounds is introduced into the system 10 along with an ECG signal representative of the electrical activity of the subject's heart. The acoustic signal may be a signal produced by a microphone or transducer attached to the subject's chest or a stored signal. Similarly, the ECG signal may be a signal produced by an electrocardiogram device attached to the subject or a stored ECG signal.

The ECG signal is passed through a first conditioning circuit 16 to form a calibration or timing signal having a QRS spike at the onset of each systolic portion in a heart pattern. The MCG signal is passed through a second conditioning circuit 14 for removing unwanted noise and amplification of low frequency sounds.

The conditioned ECG signal and the conditioned acoustic signals are introduced into the microprocessor 18. In the microprocessor, the acoustic signals are processed to obtain a real-time spectral pattern of heart sounds and the spectral pattern is matched with the calibration or timing signal. The resulting output from the microprocessor is a simultaneous display of the spectral pattern with an ECG signal, preferably in a synchronized manner.

The system of the present invention lends itself to use in a variety of different ways. For example, it is known that turbulent blood flow energy starts at approximately 300 Hz and proceeds upward to approximately 4000 Hz in the case of prosthetic and natural valves. Therefore, if desired, the video display can be color coded to facilitate the operator's interpretation of the output signals. For example, horizontal time base lines and the ECG calibration spike which appears above and behind the spectral pattern may be colored yellow/line. Energy frequencies below 300 Hz may appear as green or "good" or "go" energy. Energy frequencies above 301 Hz may appear as red or "bad" or "no-go" suspect energies which are graphic representations of turbulent blood leaking back through the heart valve. RMS sound pressure intensity can be represented as shades of either green or red frequencies. Thus, as the intensity of the "good" green energy gets higher, the shade of green gets darker. This would aid an user in intuitively recognizing amplitude differences between a series of heart beats and from patient to patient differences.

Figure 8:
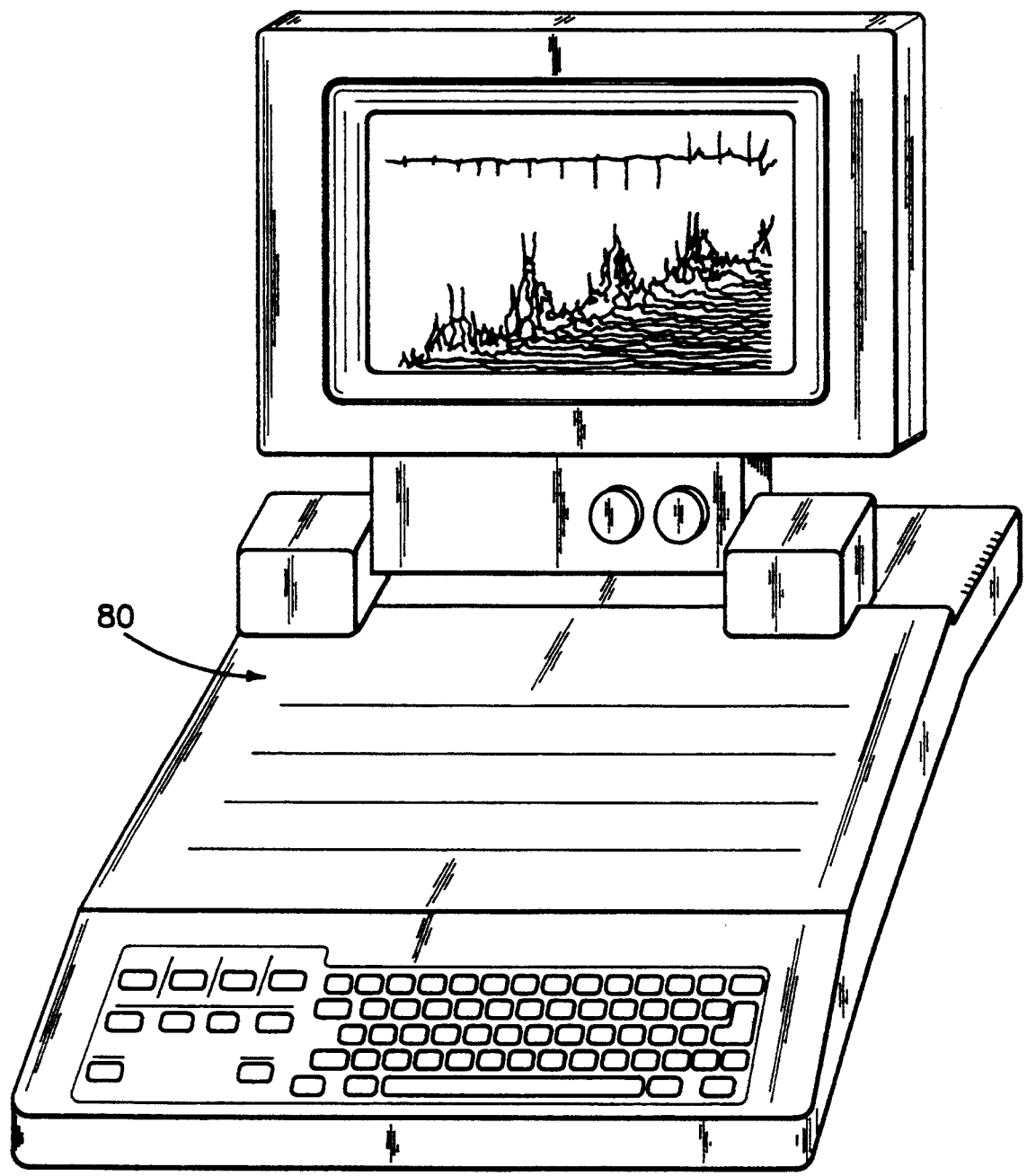
FIG. 8 illustrates a portable system embodying the system of the present invention.

As shown in FIG. 8, the system 10 may be incorporated into a portable unit 80. The unit may be in the nature of a lap top computer. Such a unit is desirable in that it can be used bedside in a hospital or clinic or in a physician's office. It should also be recognized that the unit may take the form of a desk top unit or may be placed on a cart for ease of movement.

If desired, the microprocessor 18 can be configured to allow the operator to produce a zoom picture of a desired heart sound spectra. This would involve freezing the real time scrolling spectra, picking the spectra in question to be examined and reprocessing the digital information through the microprocessor to enlarge the individual spectra to the full size of the video screen for detailed analysis of the timing and frequency content of a heart sound.

The microprocessor may also be programmed to allow an operator, through keyboard controls, a joystick or some other control device, to rotate the three dimensional spectra on the video screen to any desired viewing angle. This multiple angle viewing approach allows the operator to pick the optimum viewing angle for obtaining key frequency and timing data.

If desired, historical information stored in the storage device 68 may be recalled and displayed on the video display 62 along with a current or real time display. This can be accomplished by using known screen splitting techniques or by superimposing one image over the other to highlight differences.

Additionally, the system 10 may include a telephone modem (not shown) and a facsimile device (not shown), either separated or built-in, to send patient data from one location to another in a a rapid manner. This would provide a rapid means of obtaining second opinions or sending patient history filed to another physician in cases of vacation, emergencies or other away-from-home incidents.

While it is preferred to display the spectral pattern of the heart sounds and an ECG signal in a synchronized manner, the synchronization may be omitted if one desires.

The system 10 of the present invention also lends itself to automated diagnosis of a subject's heart condition. For example, the microprocessor 18 may be programmed to derive a parametric model of the time-frequency pattern of the heartbeat. The numeric dimensions of such a model should reflect the hemodynamics of the heart. The parameters of the model should:

(a) describe the heart sound as a function of frequency, amplitude and beat time, with several independent parameters;

(b) differentiate between normal patterns and abnormal patterns; and (c) adjust to acceptable variations in the normal heartbeat.

The time-frequency patterns of hearts known to have a specific pathology may be measured and the parameters of the above model for those hearts may be estimated. The parameters of the normal hearts in a multidimensional parameter space may be plotted with one dimension for each parameter of the model. The parameters of the abnormal hearts in the same space may also be plotted. A matrix of the Euclidean distances between the points in the parameter space is built, where each distance is the sum of the squares of the differences in the parameters, scaled by the deviations of the parameters. The elements in the matrix may be ranked to identify the clusters of points in the parameter space. The center and radius of each of the clusters associated with a particular pathology may then be described. When the loci of the clusters have been identified, the following procedure may be used to evaluate an undiagnosed beat:

(a) fit the received data to the model, by estimating its parameters, using any regression technique shown to be robust;

(b) determine the distance of the received point form the various pathology clusters; and (c) the received point then can be evaluated by deciding the cluster to which it is closest, and the likelihood of its being associated with that cluster can be measured by determining its distance from that cluster in units of standard deviation. Another method of automated diagnosis and grading of defects which may be used is as follows:

1. establish a digital library of normal heart sounds as well as murmurs, stenosis and any other heart defects which cause turbulent blood flow, and in turn abnormal acoustic outputs;

2. categorize the indicative spectral patterns for each defect and, by means of a summing technique, average the patterns together until a composite profile for each defect is established. Also, establish a composite profile for normal heart sounds by the same averaging technique; and 3. store the composite profiles for each defect on a hard drive of the microprocessor or any suitable digital storage and retrieval device. Once a patient has had their heart sounds analyzed and captured, the microprocessor can perform the same averaging technique on a number of the patients heart sounds to establish a profile. The computer will automatically compare the patient's heart sound spectral patterns to the stored normal and abnormal heart spectra library to find the best "fit" and thus establish a diagnosis. The best "fit" is done by a mathematical overlay technique where the spectral patterns are compared over the time, frequency and amplitude domains for the percentage "overlap" or energy they have in common and percentage "not overlapped" or energy they do not have in common. This would result in an overall index or ratio of "fit" energy to "not fit" energy and threshhold levels for correlation and non-correlation will determine if the computer has found a match to known a defect or a normal heart spectral pattern. E.g., a ratio of 95% fit energy to 5% nonfit energy would result in a high likelihood of the computer finding a match between spectral patterns. A 60% fit to 40% non fit would cause the computer to keep searching for a better fit, if any.

It is apparent that there has been provided in accordance with this invention a system and a process for simultaneously producing and synchronizing spectral patterns of heart sounds and an ECG signal which fully satisfy the objects, means and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A system for detecting a condition of a subject's heart, said system comprising:

means for providing an input acoustic blood flow signal;

means for providing an input signal representative of electrical activity in said subject's heart;

means for converting said acoustic blood flow signal into a signal representing a spectral pattern of heart sounds; and means for synchronizing said spectral pattern signal with said signal representative of electrical activity, whereby said spectral pattern signal synchronized with said signal representative of electrical activity is used to detect, assess, grade and diagnose the condition of said heart.

2. The system of claim 1 further comprising means for conditioning said input electrical activity signal so as to produce a calibration signal having spikes at each onset of a systolic portion of a subject's heartbeat.

3. The system of claim 2 wherein said conditioning means comprises means for amplifying the input electrical activity signal and for suppressing and rejecting noise and harmonics from the input electrical activity signal, filter means for cutting off all signal noise above a desired level in said amplified input electrical activity signal, and differentiation and rectification means for removing noise and low voltage potential and for suppressing a negative component to the input electrical activity signal so as to generate said calibration signal.

4. The system of claim 2 further comprising means for conditioning said input acoustic blood flow signal to filter out unwanted background noise and highlight low frequency portions of the heart sounds.

5. The system of claim 4 wherein said input acoustic blood flow signal conditioning means comprises a filter-/amplification device and a 20-pole Butterworth filter.

6. The system of claim 4 wherein said converting means and said synchronizing means comprise a microprocessor which receives said conditioned input acoustic blood flow signal and said calibration signal.

7. The system of claim 6 wherein said microprocessor includes digital signal processing means for producing said spectral pattern of heart sounds from said conditioned input acoustic blood flow signal.

8. The system of claim 7 wherein said microprocessor has timing logic means for matching an onset of an acoustic first heart sound of said spectral pattern with a first spike in said calibration signal.

9. The system of claim 8 wherein said microprocessor has means for automatically calculating the subject's heart rate by counting said spectral pattern heart sounds.

10. The system of claim 8 wherein said microprocessor includes means for making a preliminary diagnosis of a subject's condition.

11. The system of claim 8 further comprising an output device for receiving and displaying said spectral pattern of heart sounds synchronized with said signal representative of electrical activity.

12. The system of claim 11 wherein said output device comprises a video monitor.

13. The system of claim 11 wherein said output device comprises a printer.

14. The system of claim 8 further comprising means for storing said spectral pattern synchronized with said signal representative of said electrical activity.

15. The system of claim 8 further comprising means for inputting an unconditioned signal representative of said electrical activity in said subject's heart into said microprocessor and for matching said unconditioned signal with said onset of said acoustic first heart sound.

16. The system of claim 11 further comprising means for allowing a user to listen to said acoustic blood flow signal while viewing said output device.

17. The system of claim 1 wherein said input acoustic signal providing means comprises at least one of a microphone and a transducer adapted to be attached to the subject.

18. The system of claim 1 wherein said input acoustic signal providing means comprises an acoustic signal stored in a storage device.

19. The system of claim 1 wherein said means for providing an electrical activity input signal comprises an electrocardiograph adapted to be attached to said subject.

20. The system of claim 1 wherein said means for providing an electrical activity input signal comprises an ECG signal stored in a storage device.

21. A process for detecting a condition of a human heart comprising the steps of:
providing a first acoustic signal representative of the heart's sounds;
providing a second signal representative of electrical activity in said heart;
conditioning said second signal to obtain a calibration signal having a spike at each onset of systolic cycle in the heart;
processing the first acoustic signal to form a spectral pattern of heart sounds; and
generating a simultaneous display of said spectral pattern and a wave signal indicative of electrical activity in said heart, said generating step including matching said spectral pattern with said calibration signal,
whereby said simultaneous display is used to detect and diagnose the condition of a human heart.

22. The process of claim 21 further comprising conditioning said first acoustic signal to remove unwanted noise and highlight low frequency portions of said first acoustic signal.

23. The process of claim 21 wherein said conditioning step comprises amplifying said second signal to a desired level, filtering out unwanted information from said second signal and cutting off all signal noise above a desired level, and differentiating and rectifying said second signal after said filtering step to remove noise and low voltage potential from said second signal and to suppress a negative component to said second signal.

24. The process of claim 21 further comprising displaying said simultaneous display on a video monitor.

25. The process of claim 24 further comprising providing means for an operator to listen to the heart sounds during said displaying step.

26. The process of claim 21 further comprising printing said simultaneous display on a printer.

27. The process of claim 21 further comprising storing said simultaneous display on a storage device.

28. A system for detecting a condition of a human subject's heart, said system comprising:
means for providing an acoustic signal representative of blood flow in said heart;
means for providing a signal indicative of electrical activity of said heart; and
means for simultaneously preventing a wave pattern representative of sounds in said heart and a synchronized wave pattern of the electrical activity in said heart,
whereby said simultaneously presented wave pattern representative of sounds in the heart and said synchronized wave pattern of the electrical activity in the heart are used to detect, assess and diagnose the condition of said heart.

29. The system of claim 28 further comprising:
means for forming a calibration signal having spikes at each onset of a systolic portion of a cycle of said subject's heart from said electrical activity signal.

30. The system of claim 29 further comprising means for converting said acoustic signal into said heart sound wave pattern and for matching said converted signal with said calibration signal.

* * * * *